(12) United States Patent
Gavriely

(10) Patent No.: US 11,110,486 B2
(45) Date of Patent: Sep. 7, 2021

(54) DISINFECTANT APPLICATOR DEVICE WITH CONTOURED ROLLER

(71) Applicant: ONEG HAKARMEL LTD, Tirat Hakarmel (IL)

(72) Inventor: Noam Gavriely, Haifa (IL)

(*) Notice: Subject to any disclaimer, the term of this patent is extended or adjusted under 35 U.S.C. 154(b) by 0 days.

(21) Appl. No.: 17/272,749

(22) PCT Filed: Aug. 15, 2019

(86) PCT No.: PCT/IB2019/056923
§ 371 (c)(1),
(2) Date: Mar. 2, 2021

(87) PCT Pub. No.: WO2020/049386
PCT Pub. Date: Mar. 12, 2020

(65) Prior Publication Data
US 2021/0205838 A1 Jul. 8, 2021

Related U.S. Application Data

(60) Provisional application No. 62/726,753, filed on Sep. 4, 2018.

(51) Int. Cl.
*B05C 17/03* (2006.01)
*B05C 17/02* (2006.01)
*A61L 2/26* (2006.01)
*A61L 2/00* (2006.01)
*A45D 34/04* (2006.01)
*A61M 35/00* (2006.01)

(52) U.S. Cl.
CPC ........ *B05C 17/0325* (2013.01); *A45D 34/041* (2013.01); *A61L 2/0088* (2013.01); *A61L 2/26* (2013.01); *A61M 35/003* (2013.01); *B05C 17/0212* (2013.01); *B05C 17/0217* (2013.01); *A45D 2200/1036* (2013.01); *B05C 17/022* (2013.01); *B05C 17/0215* (2013.01); *B05C 17/0237* (2013.01)

(58) Field of Classification Search
CPC ............ B05C 17/0325; B05C 17/0212; B05C 17/0217; B05C 17/0215; B05C 17/0237; B05C 17/022; B05C 17/02; B05C 17/0207; B05C 17/0227; B05C 17/0232; B05C 17/0245; B05C 17/025; A45D 34/041; A45D 40/261; A45D 2200/1036; A61M 35/003; A61M 35/006; A61L 2/26; A61L 2/0088
USPC ............................... 401/9–11, 208, 218–220
See application file for complete search history.

(56) References Cited

U.S. PATENT DOCUMENTS 7,806,612 B1 * 10/2010 Wangler ............. A46B 11/0024
401/11
8,171,595 B1 * 5/2012 Umhoefer, Jr. ..... B05C 17/0207
15/230.11

(Continued)

FOREIGN PATENT DOCUMENTS

JP 2004066215 3/2004

*Primary Examiner* — David J Walczak
(74) *Attorney, Agent, or Firm* — Mark David Torche; Patwrite Law

(57) ABSTRACT

A liquid disinfectant applicator device, the device includes: a frame, a pair of axle portions that are movable coupled to the frame at varying angles therebetween, an absorbable roller rotatably mounted on the pair of axle portions, a sealed resilient container, at least one conduit and a perforated plate.

20 Claims, 13 Drawing Sheets

(56) References Cited

U.S. PATENT DOCUMENTS

| | | |
|---|---|---|
| 9,333,528 B2 * | 5/2016 | DeCarr .............. B05C 17/0212 |
| 2004/0101346 A1 | 5/2004 | Coombs |
| 2013/0056016 A1 | 3/2013 | Guay et al. |
| 2015/0296957 A1 | 10/2015 | Megaro et al. |
| 2016/0158792 A1 | 6/2016 | Frenkel et al. |
| 2018/0255905 A1 | 9/2018 | Choi et al. |

* cited by examiner

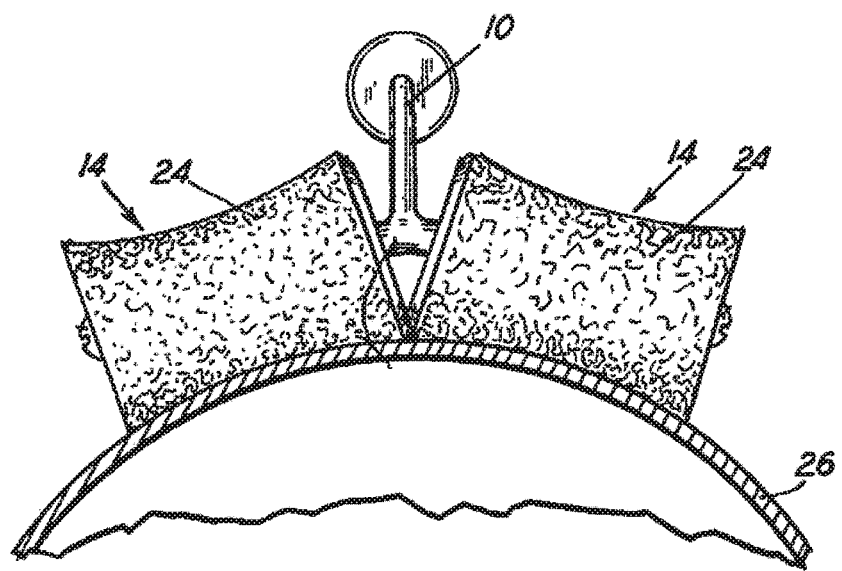
FIG. 1 – Prior Art
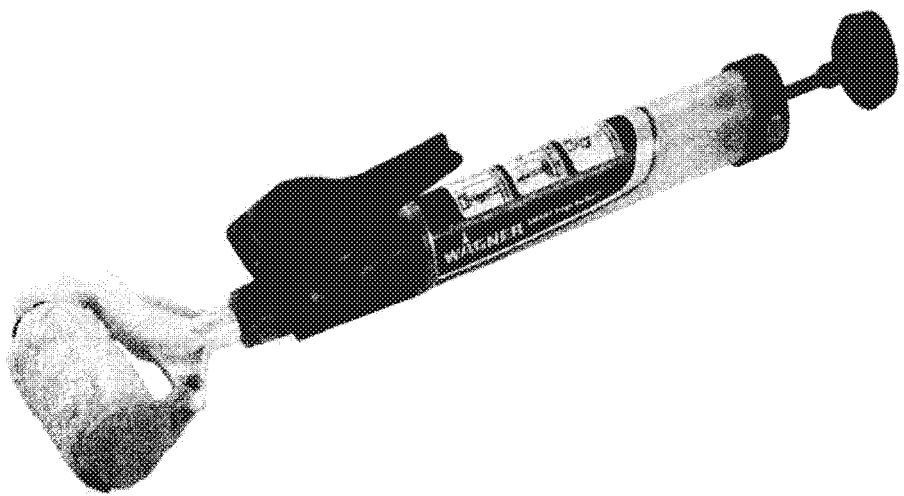
FIG. 1B – Prior Art

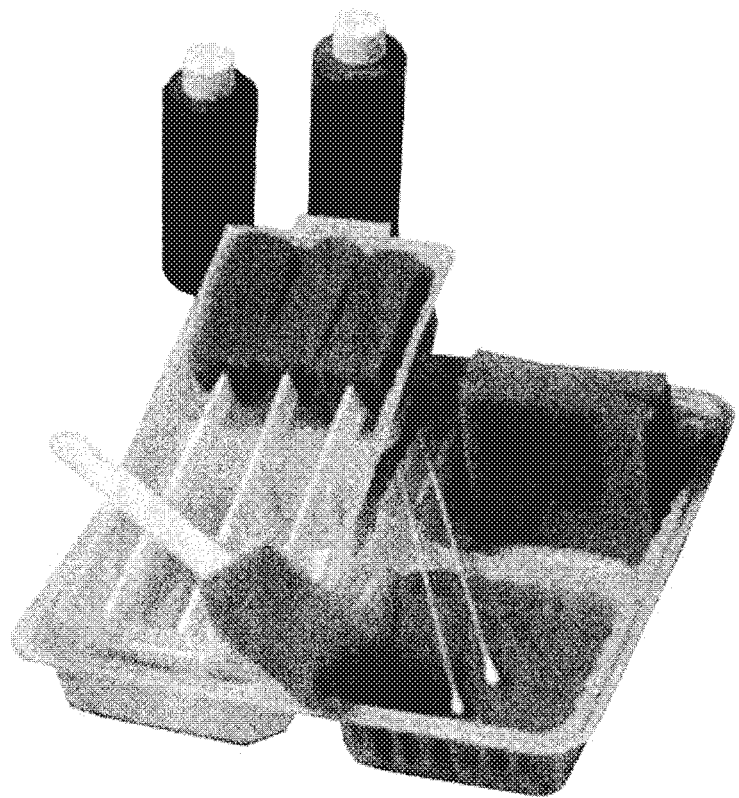
FIG. 1C – Prior Art
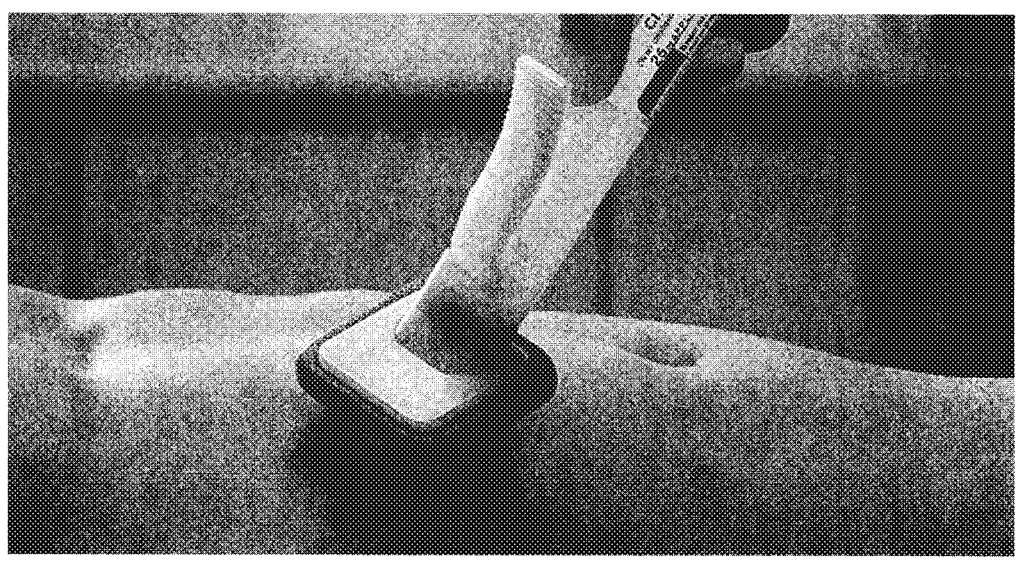
FIG. 1D – Prior Art

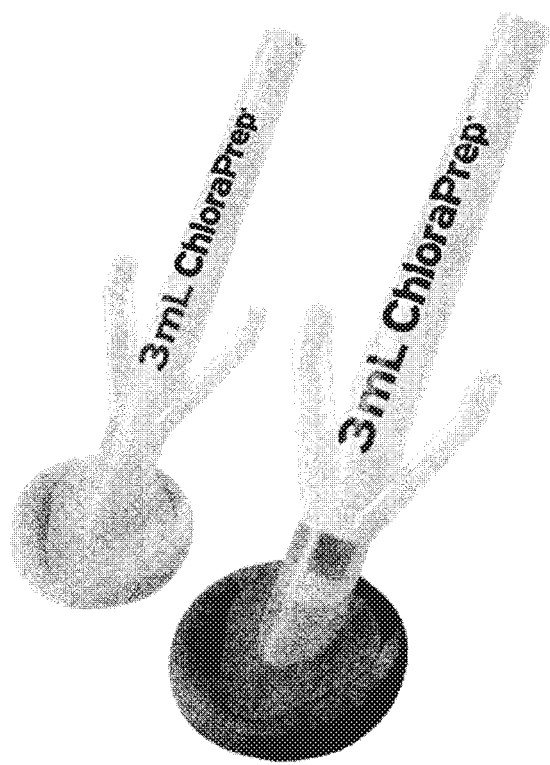
FIG. 1E – Prior Art
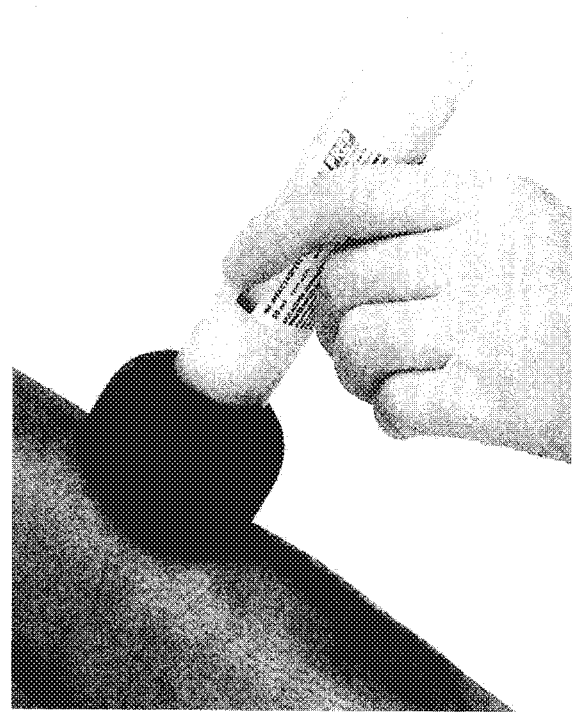
FIG. 1F – Prior Art

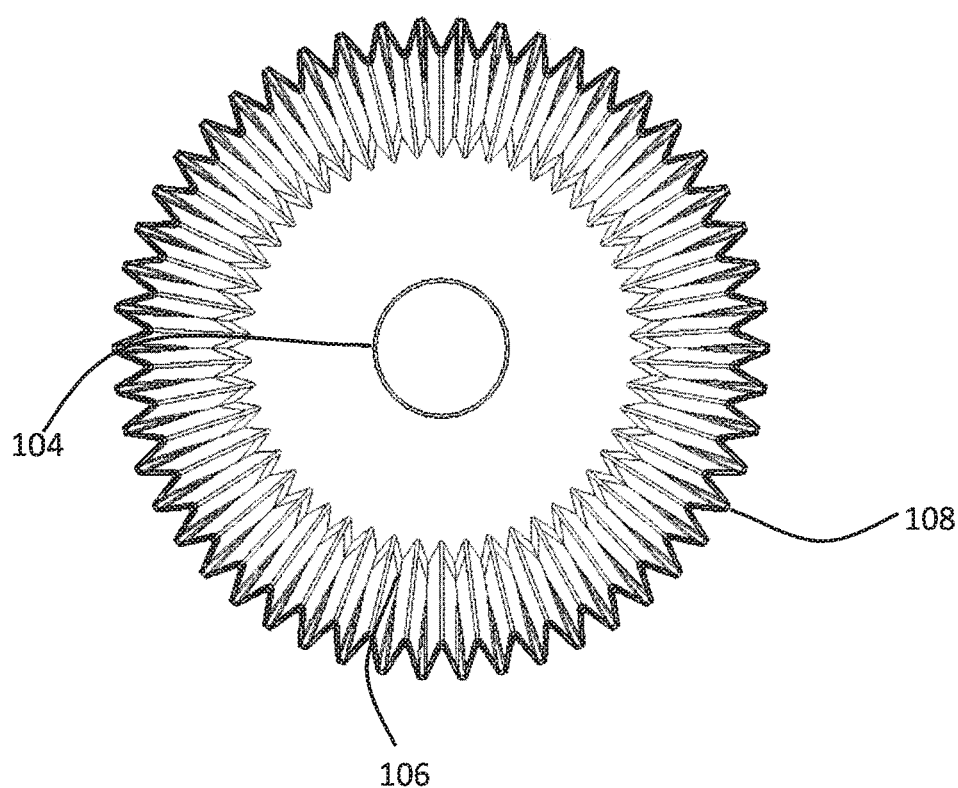
FIG. 8A
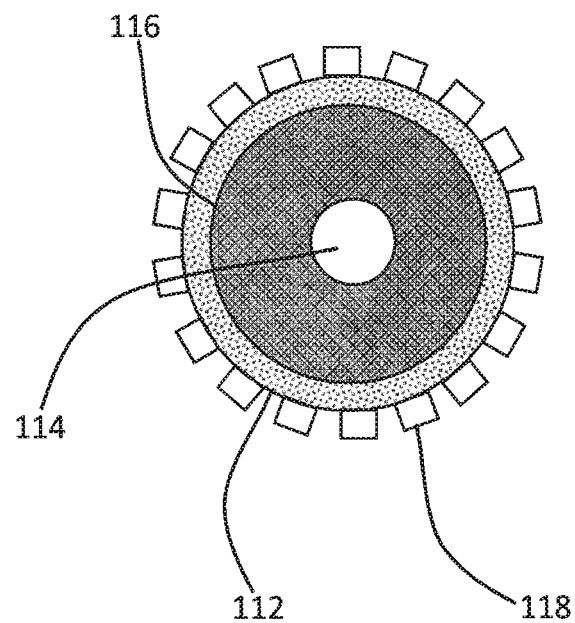
FIG. 8B
FIG. 8C

DISINFECTANT APPLICATOR DEVICE WITH CONTOURED ROLLER

TECHNICAL FIELD

The present invention generally relates to devices and methods for applying liquids to non-planar surfaces. More particularly, the invention relates to applicator devices that are configured to apply a relatively thin layer of liquid (e.g., a liquid medicament) to curved skin surfaces of a patient from a sterile reservoir of the liquid.

BACKGROUND ART

It is believed that the current state-of-the-art is described by the following patent literature: U.S. Pat. Nos. 4,167,349, 4,723,860, 5,213,431, 5,564,851, 6,017,162, 6,543,950, 6,857,806, 8,123,423, 8,382,727, 9,498,610, EP2744364, GB2495295 and CN205287231.

It is believed that the current state-of-the-art is described by the following non-patent literature:

Moisturizing Mate Lotion Applicator, available at the following URL: https://web.archive.org/web/20121211005642/https://www.amazon.com/Moisturizing-Mate-Lotion-Applicator/dp/B008U1AW18 and/or Ableware Roll Easy Lotion Applicator available at the following URL: https://web.archive.org/web/20190708113753/https://www.amazon.in/Ableware-Roll-Easy-Lotion-Applicator/dp/B000TYO1TS/ref=pd_sim_328_1?_encoding=UTF8&psc=1&refRID=N32YFGWEZWJ0CVC9E3MN and/or BIOAQUA BB Cream Roller Miracle Skin Perfect BB Cream Anti-Aging Foundation with Thin Concealer CC Cream available at the following URL: https://web.archive.org/save/https://www.amazon.com/BIOAQUA-Miracle-Anti-Aging-Foundation-Concealer/dp/B077PVJPF8.

Spreading liquid on a surface is typically done with a brush, sponge, cloth, sprayer or a roller, and is a well-known process in construction/renovation and healthcare. For example, straight and curved rollers for painting walls and flat surfaces, as well as curved surfaces such as columns and rounded walls, are well known. For example, U.S. Pat. No. 2,881,461 to Wynton E. Parker discloses a paint applicator for applying paint to a curved surface of a pipe or similar article, as shown in FIG. 1A. The paint applicator includes a handle 10, a pair of opposite oblique axle portions, and a pair of concave rollers 14 rotatably mounted the axle portions. The outer surface 24 of each roller is shaped as a fixed curved surface such that the intersection of the surfaces with a plane containing the axis of the rollers defines a fixed arc 26 of a predetermined radius. The axle portions extend at an angle to one another such that a plane containing the axes thereof and intersecting the points of contact between the rollers intersects the rollers along a substantially continuous fixed arc 26 defined by the predetermined radius. Another prior paint applicator, the SMART Edge Roller sold by Wagner SprayTech Corp. of Minneapolis, Minn., USA, is shown in FIG. 1B. As shown in FIG. 1B, the SMART Edge Roller paint applicator includes a flat roller in communication with a rigid cylindrical paint reservoir that holds a volume of paint. The paint reservoir includes a manually operated plunger used to draw paint into the reservoir, and an associated trigger that delivers paint from the reservoir to the interior of the roller and therethrough via "pumping" of the trigger.

In healthcare, many liquid applicator devices are used to spread medicaments on the skin of a patient (e.g., a human patient). Such liquid applicator devices include sponges, with or without dispensers, for spreading lotions, creams, sun-protection chemicals and disinfecting liquids on the skin of a patient. FIGS. 1C-1F illustrate examples of such current liquid medicament applicator devices.

As shown in FIG. 1C, a kit including a tray, one or more containers of liquid medicament and sponges and/or cotton swabs for applying the liquid medicament to the skin of a patient is often utilized. In this example, the liquid medicament is typically poured into the tray, and a swab or sponge is dipped in the liquid and then spread on the skin. Other typical current liquid medicament applicator devices comprise a sponge connected to and in communication with an end of a container containing disinfecting fluid, as shown in FIGS. 1D and 1E. The container is used as a handle for moving the sponge on the skin of a patient. These devices include a trigger, as shown in FIGS. 1D and 1E, that breaks or opens an ampule or other sealed portion within the container that contains the disinfecting fluid. Once the sealed portion is broken, pierced or otherwise opened via the trigger, the sterile disinfecting fluid flows therefrom and into the associated sponge. These devices thereby provide for a single dose of a predetermined volume of disinfecting fluid to the sponge, and thereby to the skin of the patient. If additional disinfecting fluid is needed, another device must be used.

Another current liquid medicament applicator device that includes a sponge connected to and in communication with an end of a container containing disinfecting fluid that is used as a handle for moving the sponge on the skin of a patient is shown in FIG. 1F. The liquid medicament applicator device of FIG. 1F is configured to dispense the disinfecting fluid within the container via the user manually squeezing or deforming the container to force some of the disinfecting fluid through a valve, port or other passageway and into the sponge (i.e., make the reservoir containing the disinfecting fluid smaller). After some of the disinfecting fluid is dispensed, the user stops squeezing or otherwise deforming the container to allow the container to elastically deform or otherwise expand back to its natural shape, size or other configuration (i.e., make the reservoir containing the disinfecting fluid larger), and thereby create a vacuum (i.e., negative pressure) therein that draws or sucks air, and thereby microorganisms contained therein, into the container that replaces the dispensed volume of disinfecting fluid.

Current liquid applicator devices, including current liquid medicament applicator devices, are thereby lacking in several major aspects. For example, the devices are inefficient and time-consuming. As another example, the devices do not provide uniform coverage of the liquid applied to the surface of the skin of the patient. Still further, the devices do not conform to the curvature of the surface onto which the liquid (e.g., liquid medicament) is applied. As yet another example, devices only allow either rolling or spreading/dragging of the liquid via the applicator member (i.e., a roller or sponge/pad). Still further, the devices fail to maintain the sterility of the liquid inside the dispensing reservoir thereof. For example, the devices do not maintain separation of the liquid inside the dispensing reservoir from ambient air to avoid contamination or chemical reaction caused by the mixing of the liquid with the air (i.e., to not keep the dispensing reservoir airtight at all times).

Therefore, a need exists for improved liquid applicator devices, including current liquid medicament applicator devices. While certain aspects of conventional technologies have been discussed to facilitate disclosure of the invention, Applicants in no way disclaim these technical aspects, and it is contemplated that the claimed invention may encompass one or more of the conventional technical aspects discussed herein.

SUMMARY OF THE INVENTION

Briefly, the present inventions satisfy the need for improved liquid applicator devices, liquid medicament applicator devices and related methods. The present inventions may address one or more of the problems and deficiencies of the art discussed above. However, it is contemplated that the inventions may prove useful in addressing other problems and deficiencies in a number of technical areas. Therefore, the claimed inventions should not necessarily be construed as limited to addressing any of the particular problems or deficiencies discussed herein.

Certain embodiments of the presently-disclosed liquid applicator devices, liquid medicament applicator devices and related methods have several features, no single one of which is solely responsible for their desirable attributes. Without limiting the scope of the liquid applicator devices, liquid medicament applicator devices and related methods as defined by the claims that follow, their more prominent features will now be discussed briefly. After considering this discussion, and particularly after reading the section of this specification entitled "Detailed Description," one will understand how the features of the various embodiments disclosed herein provide a number of advantages over the current state of the art The present disclosure, in some embodiments, provides liquid (medicament) applicator devices and related methods configured to uniformly spread a liquid on a surface, whether flat or curved/arcuate, while preventing the liquid from contact with ambient air (and its contaminants and oxygen) within the liquid reservoir of the device before being applied to the surface (i.e., applied to a roller, or a pathway extending to the roller, of the device which applies the liquid). In some embodiments, the liquid (medicament) applicator devices and related methods include a cylindrical or a non-cylindrical roller made from open-cell foam or cloth or other absorbent materials. In some embodiments, the liquid (medicament) applicator devices and related methods include a frame with two hinges of varying/selectable angles on which the roller is supported and rotates/rolls. In some embodiments, the liquid (medicament) applicator devices and related methods include a perforated plate associated with the frame that includes a plurality of openings or holes proximate to the roller (e.g., aimed in the direction of the roller) and connected to or in fluid communication (such as via a one-way valve) with a sterile liquid (medicament) reservoir that contains a liquid (medicament), via one or more conduits, located within an elastically deformable container-handle of the device. In some such embodiments, the reservoir is deformed, pressed or compressed (e.g., via deforming, pressing or compressing the container-handle), to force a flow of the liquid from the reservoir to the perforated plate, and ultimately through the openings in the perforated plate (e.g., sprayed) and onto the outer surface of the roller. In some such embodiments, the container-handle of the liquid (medicament) applicator devices and related methods that include the liquid (medicament) reservoir also include a flexible bag, bladder, container or vessel positioned at least partially therein that is expandable (and thereby also collapsible). In such embodiments, the container-handle may be sealed and the collapsible bag may be formed of a flexible, non-permeable material or wall that forms or defined an inner cavity or space that is air-tightly connected (i.e., sealed) to a one-way valve that extends through the container-handle. The one-way valve is configured to allow air to enter into the sealed bag (i.e., expand the bag) to allow the bag to expands and thereby replenish or fill a volume within the container/reservoir that was previously occupied by liquid (medicament) which was expelled from the reservoir within the container-handle (e.g., via compression or collapse thereof) so that the container-handle is able to elastically deform back to its neutral or natural shape/size and, thereby, the total neutral or natural volume inside the container-handle is restored (and the (volume of the) reservoir is effectively shrunk or reduced). In this way, a plurality of discrete doses or amounts of liquid (medicament) can be dispensed from the reservoir of the container-handle over a period of time, and the sterility of the liquid (medicament) may be maintained during the entirety of the period of time.

In one aspect, the disclosure provides liquid (medicament) applicator devices and related methods for uniformly spreading a liquid on a curved, arcuate or non-planar surface. The devices and methods comprise a serrated surface roller with varying curvilinear contours that conforms to the curvature of the surface it is positioned on or abuts, and can either roll on the curved surface or be prevented from rolling so that it can be dragged on the surface while spreading a liquid, lotion or crème of any viscosity (such as, but not limited to, a medicament).

In some embodiments, the liquid (medicament) applicator devices and related methods utilize a reservoir for sterilely containing or housing liquid that is selective fluid communication with at least one conduit (e.g., a plurality of conduits) that fluidly connects the reservoir to a perforated plate. In some embodiments, the perforated plate may be curved, such including a radius of curvature that extends substantially parallel to that of the outer surface of the roller. In one embodiment, the devices may include a container that at least partially forms or contains the liquid reservoir within an internal cavity thereof. The container may also form as a manually-engageable handle of the device for manually using the roller of the device to apply or spread the liquid in the reservoir on at least the curved surface, such as a curved portion of the skin of a patient. The container forming or housing the reservoir within an internal cavity thereof may be manually elastically deformable (e.g., constructed from a manually elastically deformable or squeezable material) such that, when compressed (i.e., force the internal cavity to become smaller), forces or expels the liquid from said reservoir, through the at least one conduit, and to and through the perforated plate onto the outer surface of the roller. The container/reservoir may thereby be constructed from a material that, when not squeezed, will elastically re-expand or deform to its natural, neutral or original shape// size (and the natural, neutral or original volume of the internal cavity thereof) by its own resiliency or recoil properties.

In some embodiments, the liquid (medicament) applicator devices and related methods may be configured to maintain the sterility of the liquid (medicament) within the internal reservoir of the container, such as by preventing contact of the liquid (medicament) within the reservoir of the container from with air entering the container/fluid reservoir when the container naturally resiliently or elastically expands/deforms after manual compression/deformation thereof to replenish the volume therein previously occupied by the of the volume of fluid that was immediately previously expressed or delivered onto the roller. For example, in some embodiments the container may include at least a pair of one-way valves extending therethrough. The pair of one-way valves may include at least one dispensing one-way valve, positioned proximate to the roller, that is in direct or fluid communication with the sealed internal cavity of the container which forms the fluid reservoir. The at least one dispensing one-way valve is thereby in direct or fluid communication with the fluid reservoir. The at least one dispensing one-way valve may be configured to only allow the liquid within the reservoir to flow in the direction out of the reservoir and toward the roller. For example, the at least one dispensing one-way valve may be in communication with at least one conduit or channel that deliver the dispense liquid to the roller. The at least one dispensing one-way valve may thereby be configured to prevent the flow or migration of any air, liquid or any other material therethrough into the reservoir/internal cavity of the container from exterior thereof (i.e., in the opposing direction as the flow of the liquid from within the reservoir/internal cavity of the container to exterior to the reservoir/internal cavity) (during normal or typical operation or use of the device) so as to maintain the sterility of the internal cavity/reservoir.

The pair of one-way valves may also include at least one intake, refill or replacement air one-way valve, positioned distal to the roller, that extends into the sealed internal cavity of the container which forms the fluid reservoir and the environment (i.e., air) exterior to the container. The at least one intake one-way valve may thereby extend into the fluid reservoir. However, the at least one one-way intake valve may not be in fluid or direct communication with the reservoir/internal cavity. Instead, the at least one one-way intake valve may be in fluid or direct communication with a deformable (e.g., expandable and collapsible) non-permeable flexible-wall bag, bladder or vessel positioned within the internal cavity of the container. The collapsible bag may be sealed to the at least one one-way intake valve so as to form a sealed space, partition, cavity or bag positioned within the internal cavity and in communication with the least one one-way intake valve.

The reservoir may thereby comprise or be defined by the space or volume within the internal cavity of the container that extends or is positioned about or around the expandable intake bag. Stated differently, the reservoir may comprise or be formed of the open space or volume within/of the internal cavity of the container that is defined by the inner surfaces of the container and the outer surfaces of the expandable intake bag (and potentially the outer surfaces of the valves). However, the at least one one-way intake valve may extend through the container such that it is communication with the environment (e.g., air), and is configured to only allow the environment exterior of the internal cavity to flow into the expandable intake bag (and thereby into the internal cavity). The at least one one-way intake valve may thereby be configured to prevent the flow or migration of any air, liquid or any other material therethrough from within the expandable intake bag to the environment exterior of the internal cavity. However, in some other embodiments, the rather than including the at least one one-way intake valve, the device may include an aperture or valve that allows air or any other material from flowing into the expandable intake bag from the environment exterior of the internal cavity, and out of the expandable intake bag into the environment exterior of the internal cavity.

In some embodiments, the at least one one-way intake valve may thereby allow ambient air or other material to penetrate into expandable intake bag positioned placed inside the internal cavity of the container to expand the expandable intake bag while preventing the air or other material from contacting the liquid in the reservoir portion thereof to maintain the sterility thereof. In this way, air can replace any liquid expelled from the reservoir without forming any contact between the air and the liquid and without leak of the liquid out of the reservoir. The bag-reservoir arrangement or configuration thereby advantageously prevents contamination of the liquid within the reservoir of the internal cavity of the container by microorganisms in the air and to avoid air-induced chemical reaction between the liquid and the air.

The one-way valve is thereby also configured to allow air to enter into the sealed bag (i.e., expand the bag) to allow the bag to expands and thereby replenish or fill a volume within the container/reservoir that was previously occupied by the liquid (medicament) which was expelled from the reservoir (e.g., via compression or collapse thereof) so that the container is able to elastically deform back to its neutral or natural shape/size and, thereby, the total neutral or natural volume of the internal cavity/reservoir inside the container is restored (and the (volume of the) reservoir is effectively shrunk or reduced). The container can thereby be used as a handle of the device, and used to dispense all (or a selective amount) of the liquid from the reservoir onto/into the roller of the device. In this way, a plurality of discrete doses or amounts of liquid (medicament) can be dispensed from the reservoir of the container-handle over a period of time, and the sterility of the liquid (medicament) may be maintained during the entirety of the period of time.

In some embodiments, the roller of the liquid (medicament) applicator devices and related methods may be formed from open-cell foam material, such as but not limited to polyurethane foam. In some embodiments, the roller may be formed from a plurality of concentric elastomeric materials of different Shore (00) or Shore A levels. In one such embodiment, the inner material may include a different absorbency than the outer foam material.

In some embodiments, the outer surface or contour of the roller of the liquid (medicament) applicator devices and related methods may be concave, such as being arcuately concave (e.g., include an external contour shape following essentially the outline of a circle or an ellipse). In some other embodiments, the external contour of the roller may be parabolic. In some embodiments, the external surfaces of the roller may consist of or form recesses or troughs (and thereby raised portions or ridges therebetween) spaced or positioned about the axis of rotation of the roller, which may each be concave or parabolic along the width of the roller. In some embodiments, the outer surface of the roller may be formed of multiple protruding circular ridges that are configured to fit in between a human patient's fingers and/or toes. In some embodiments, the roller may include or define a width within the range of 1 cm to 50 cm.

In some embodiments, a pair of axes or axle portions on which the roller turns or rotates may be configured to be selectively tilted or moved so as to change or alter the angulation therebetween, and thereby bend or deform the roller along its axis when it rotates or revolves so that at its front-facing or front-most surface portion, for example, becomes more or less concave or convex.

In some embodiments, the liquid (medicament) applicator devices and related methods may include a perforated plate with hole or apertures that are in fluid communication with qt least one one-way dispensing valve. According to some embodiments, the holes of the perforated plate may be proximate to the roller and vary in diameter from 0.5 mm to 4.0 mm, such as depending of the viscosity of the liquid intended to be spread by the roller. In some embodiments, the average diameter of the holes of the perforated plate may be relatively small for low viscosity liquids such as alcohol and water, or may be relatively larger for high viscosity liquids such as lotions and cremes.

In some embodiments, the holes of the perforated plate positioned proximate, near or relatively closer to the one or more conduit defining at least one flowpath for the liquid extending from the at least one dispensing one-way valve associated with the reservoir may be smaller than holes positioned relatively further away from the one or more conduit to facilitate a substantially uniform flow (e.g. spray) of the liquid through the holes. In other some embodiments, number of holes per unit area (density) of the perforated plate that are positioned near the at least one conduit may be fewer than the number of holes per unit area (density) positioned relatively further away from the at least one conduit, such as to facilitate a substantially uniform flow (e.g. spray) of the liquid through the holes.

In some embodiments, the liquid (medicament) applicator devices and related methods may include a moveable lever that is configured to be (manually) slid forward into contact with the roller and temporarily prevent it from rotating or rolling, so that the roller must be dragged on a surface to apply the liquid in/on the roller thereto. The lever may be configured that it can be (manually) slid backwards to as to allow not interfere with the rotation of the roller (i.e., allow the roller to freely rotate or roll).

In some embodiments, the reservoir of the container of the liquid (medicament) applicator devices and related methods may initially be pre-filled with the liquid (e.g., fully filled), and the container may not be coupled to a frame or other portions of the device. The frontal one-way dispending valve may then be sealingly inserted or coupled in an opening of the container extending into the internal cavity/reservoir (e.g., via a non-permeable membrane). In some embodiments, the one-way dispensing valve may be sealed off or closed with a cap (e.g., a threaded cap). When the device is to be used, the cap may be removed from the opening of the container and the container may be coupled to a frame or other components of the device to form and utilize the device. For example, the container may be screwed into a female receptacle in a frame portion of the device. The frame portion of the device may be equipped with an internal sharp cutting protrusion so that when the reservoir is coupled into place, a membrane sealing the reservoir is perforated to create a continuity between the liquid-containing reservoir and the frame or body of the device.

In some other embodiments, the reservoir of the container of the liquid (medicament) applicator devices and related methods may be filled with the liquid when it is ready to be used. For example, the frontal one-way dispensing valve may be inserted into an opening of the reservoir, and may be immediately connected to the frame or body of the device (e.g., by screwing it into a receptacle). To avoid contamination, filling of the reservoir with the liquid (medicament) may be done in a HEPA-filtered air environment, and if air (e.g., oxygen) contact with the liquid is not desirable the filling may be done in an oxygen-free chamber.

In some embodiments, the reservoir of the container of the liquid (medicament) applicator devices and related methods may be configured to contain a relatively large volume of liquid, such as a volume sufficient to coat the skin surface (and flow to the roller of device via at least one conduit connected to the dispensing valve). In some embodiments, the flow of liquid from the reservoir of the container to the roller is driven by gravity. In some embodiments, the flow of liquid from the reservoir of the container to the roller is driven by pressure created by elastic means of a spring, a pump or by placing an external load on the flexible container (e.g., manual compression or squeezing of the container).

In some embodiments, the liquid (medicament) applicator devices and related methods may utilize and apply disinfecting fluid, such as but not limited to betadine, poldine, alcohol, germicidal detergent, chlorhexidine, any other disinfecting fluid, or a combination thereof. In some embodiments, the liquid (medicament) applicator devices and related methods may utilize and apply a liquid lotion, such as but not limited to skin lotion, sunscreen lotion, body oil or any other lotion or crème intended to be uniformly applied to the surface of the body, or a combination thereof. In some embodiments, the liquid (medicament) applicator devices and related methods may utilize and apply a liquid paint, stain, glue or adhesive.

In some embodiments, the liquid (medicament) applicator devices and related methods may utilize a frame or body that rotatable couples the roller to the container, and forms or supports the perforated plate and/or the at least one conduit extending from the at least one dispensing valve to the perforated plate. In some such embodiments, frame or body may be formed form a plastic and/or metal

DESCRIPTION OF THE DRAWINGS

The present invention will be understood and appreciated more comprehensively from the following detailed description taken in conjunction with the appended drawings in which:

FIG. 1A illustrates a prior art paint applicator device comprising a pair of curved contour rollers;

FIG. 1B illustrates a prior art paint applicator device including a paint reservoir that acts as a handle and a trigger to dispense paint from the reservoir;

FIG. 1C illustrates a prior art liquid medicament applicator kit including a tray, one or more containers of liquid medicament and sponges and/or cotton swabs;

FIG. 1D illustrates prior art liquid medicament applicator device comprising a container containing disinfecting fluid that is used as the handle of the device, a sponge connected to and in communication with an end of the container, and a trigger that permanently opens a sealed reservoir within the container that contains the disinfecting fluid when manually operated;

FIG. 1E illustrates another prior art liquid medicament applicator device comprising a container containing disinfecting fluid that is used as the handle of the device, a sponge connected to and in communication with an end of the container, and a trigger that permanently opens a sealed reservoir within the container that contains a fixed volume of disinfecting fluid when manually operated;

FIG. 1F illustrates a prior art liquid medicament applicator device comprising a sponge connected to and in communication with an end of a container-handle that contains disinfecting fluid and non-sterile air drawn from the environment therein during use;

FIG. 8A to 8C illustrate side view of exemplary roller that may be utilized with the liquid applicator device of FIG. 2 according to the present disclosure;

Figure 2:
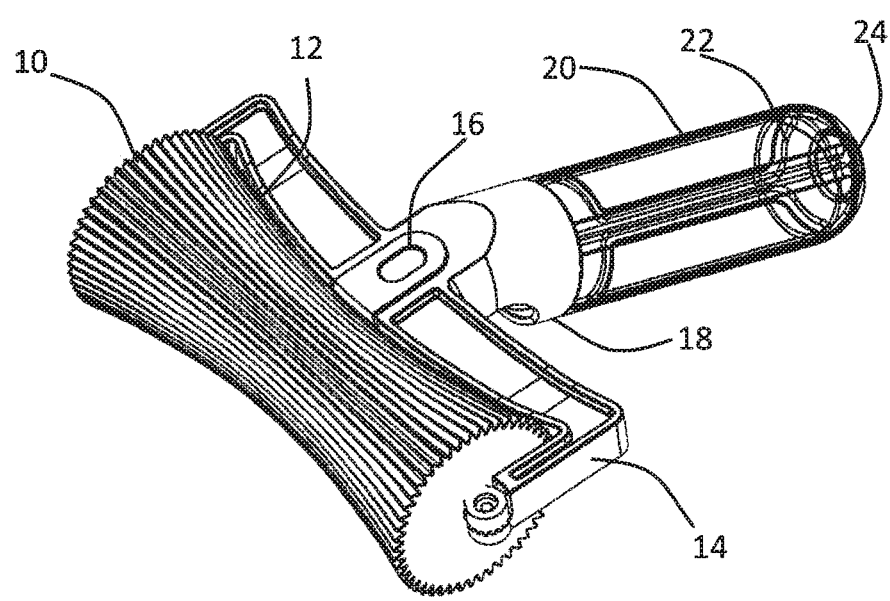
FIG. 2 illustrates an elevational perspective view of an exemplary liquid applicator device with a contoured roller according to the present disclosure.

While the invention is susceptible to various modifications and alternative forms, specific embodiments thereof have been shown merely by way of example in the drawings. The drawings are not necessarily complete and components are not essentially to scale; emphasis instead being placed upon clearly illustrating the principles underlying the present invention.

DETAILED DISCLOSURE OF EMBODIMENTS

Aspects of the present invention and certain features, advantages, and details thereof, are explained more fully below with reference to the non-limiting embodiments illustrated in the accompanying drawings. Descriptions of well-known materials, fabrication tools, processing techniques, etc., are omitted so as to not unnecessarily obscure the invention in detail. It should be understood, however, that the detailed description and the specific example(s), while indicating embodiments of the invention, are given by way of illustration only, and are not by way of limitation. Various substitutions, modifications, additions and/or arrangements within the spirit and/or scope of the underlying inventive concepts will be apparent to those skilled in the art from this disclosure. For example, before explaining embodiments of the inventions in detail, it is to be understood that the inventions are not necessarily limited in its application to the details of construction and the arrangement of the components and/or methods set forth in the following description and/or illustrated in the drawings and/or the examples (if provided). Rather, the inventions are capable of other embodiments or of being practiced or carried out in various ways that one of ordinary skill in the art would appreciate.

Figure 3:
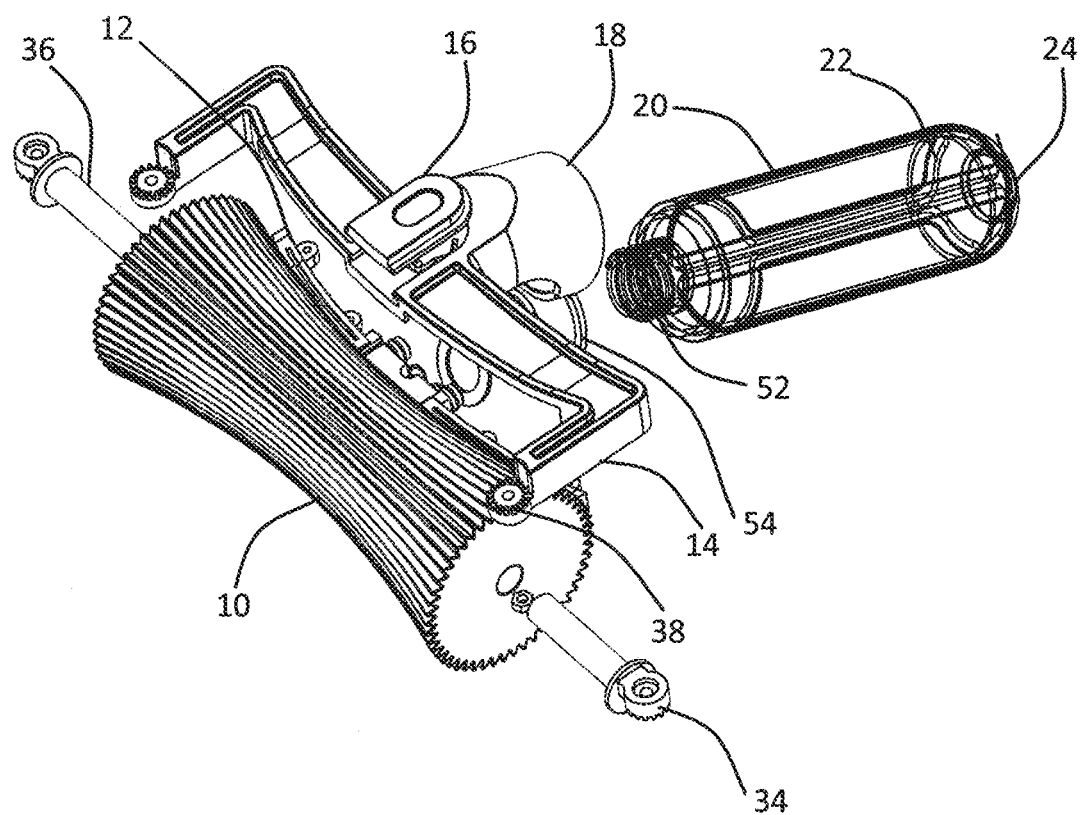
FIG. 3 illustrates an elevational perspective exploded view of the liquid applicator device of FIG. 2.
Figure 4:
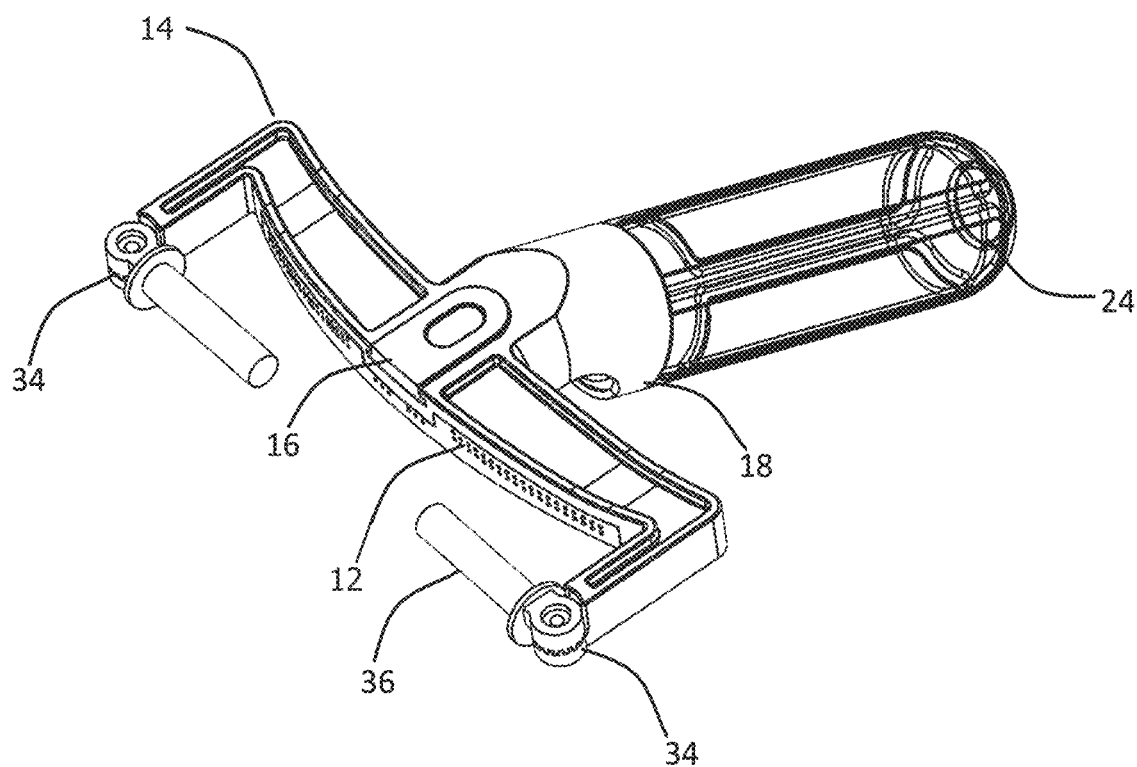
FIG. 4 illustrates an elevational perspective view of the liquid applicator device of FIG. 2 partially unassembled.

An exemplary liquid (medicament) applicator device and related method are illustrated in FIGS. 2 to 4. FIG. 2 shows the assembled device and its main components or elements. As shown in FIGS. 2 and 3, the device includes a roller 10 with a curved profile across its width and its surface is serrated, although it can also be smooth for certain applications. When the roller 10 is rotated around/about/on hinges of the device, as discussed further below, the surface of the roller 10 is in close proximity to a perforated plate 12 of the device that held in place by a frame 14 of the device, as shown in FIGS. 2 and 3.

As shown in FIGS. 2 to 4, the device may include a movable lever 16 that allows the roller 10 to rotate when retracted or positioned in a retracted position, but when pushed forward or positioned in a locking position (e.g., by sliding the lever 16 in a track), the lever 16 it comes in contact with the surface of the roller 10 and stops it from rotating. When prevented from rotating, the roller 16 is able to be wiped or dragged on a surface to spread or apply the liquid on/to a surface.

As shown in FIGS. 2 to 4, the device may include a frame 14 with a receptacle portion 18 configured to accept a container or reservoir 20. The container or reservoir 20 may include or define an internal cavity that may be filled with or otherwise contain a liquid 22, such as a medicament.

As shown in FIGS. 2 to 4, the device may include a one-way intake valve 24 that passes through and/or is in communication with the internal cavity. The intake valve 24 may be positioned in a portion of the container 20 distal to the roller 10 and perforated plate 12. The container 20 may be configured to be utilized as or form a manually-engageable handle for the device.

As shown in FIG. 3, the device may include a pair of opposing hinged or movable axle portions 36 on which the roller 10 rotates when in use (and the lever 16 is configured to allow such rotation). The axle portions 36 are coupled to the frame 14 via variable angle fasteners 34 and 38. In some embodiments, the axle portions 36 are coupled to the frame 14 via flexible coupling mechanisms or fasteners, or are themselves flexible, which may vary their orientation depending on the pressure applied by the roller 10 on a surface during use. In some other embodiments, the axle portions 36 may be coupled to the frame 14 via spring-loaded fasteners, such that when no pressure (force) is applied by the roller 10 on the surface the roller 10 returns to its neutral position with the two axles 36 facing each other.

As shown in FIGS. 2 to 4, the device may include a perforated plate 12 firmly coupled to the frame 14. The perforated plate 12 may be configured such that a front face thereof extends substantially parallel to the surface of the roller 10 (in a neutral state thereof). As shown in FIG. 3, the device may include an insert 54 with a receptacle 18 that includes internal threads corresponding to external threads 52 on a neck portion of the container 22. The container 20 may thereby be screwed into the receptacle 18 to fluidly couple them together in a substantially leak-proof manner. As shown in FIG. 3, a front-end portion of the insert 54 may be fluidly coupled or connected to perforated plate 12 via a plurality of tubes or conduits extending from the front portion of the insert 54 to nipples on the back side of the perforated plate 12. In this way, when liquid is expelled from the container 20, it flows through the insert 54 and the tubes to the perforated plate 12, and is sprayed or otherwise flows through the holes in its front aspect onto the roller 10.

As shown in FIG. 4, the variable angle fasteners 34 and 38 mounting the axle portions 36 to the frame 14 may comprise a swivel mechanism with fixed or predetermined user-selectable angular orientations, or alternatively fully variable user-selectable angular orientations. As shown in FIG. 4, the perforated plate 68 may be connected to the frame 14 such that the holes thereof face and are substantially aligned with the roller 10 when it is positioned in the axle portions 36.

Figure 5:
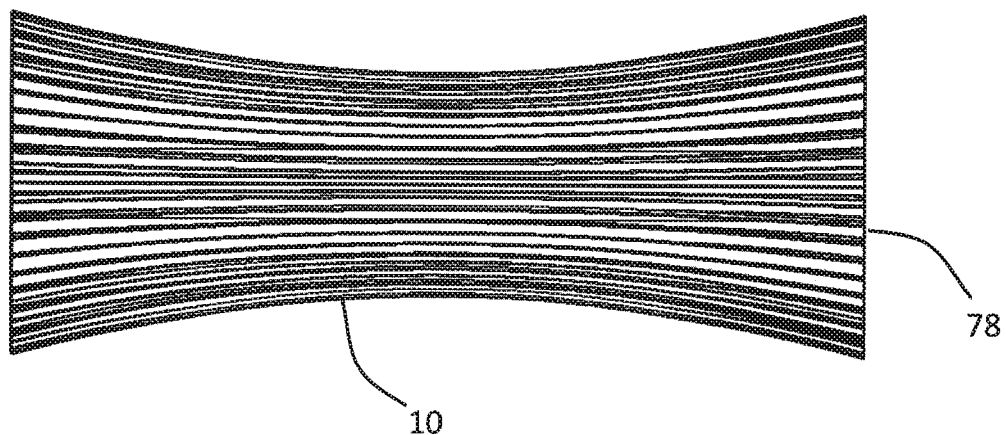
FIG. 5 illustrates an elevational perspective view of the exemplary contoured roller of the liquid applicator device of FIG. 2 according to the present disclosure.
Figure 6:
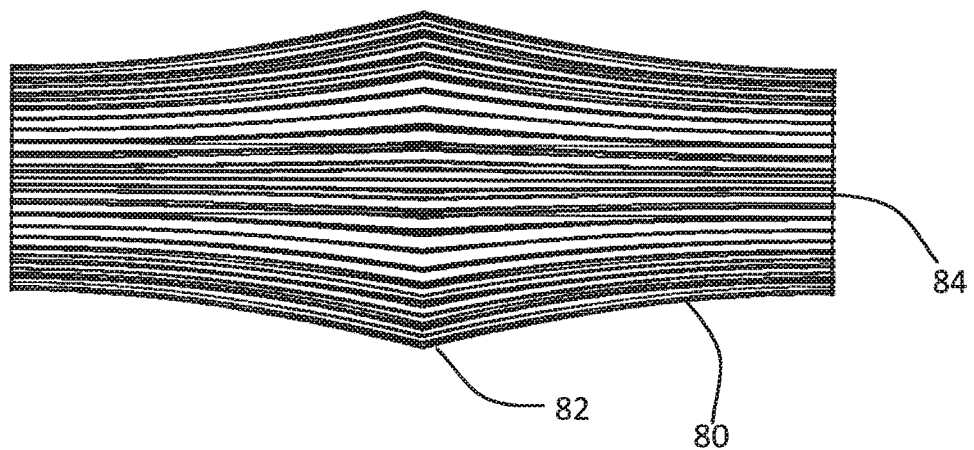
FIG. 6 illustrates an elevational perspective view of another exemplary contoured roller for the liquid applicator device of FIG. 2 according to the present disclosure.

As shown in FIG. 5, the outer surface of the roller 10 may be serrated curvilinear with its side surface 78. As understood by one or ordinary skill in the art, the shape of the roller can be of any different contour. For example, as shown in FIG. 6, the outer surface of a roller 82 may be of a picked convex shape with its side surface 84 and include serrations 80.

Figure 7A:
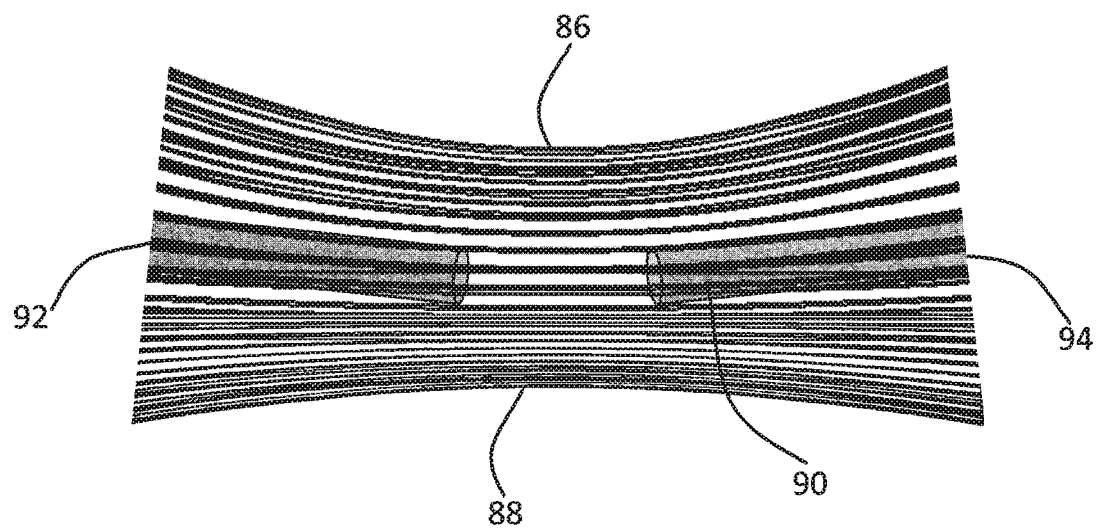
FIG. 7A illustrates a front view of the contoured roller of the liquid applicator device of FIG. 2 in an exemplary first configuration via axle portions thereof according to the present disclosure.
Figure 7B:
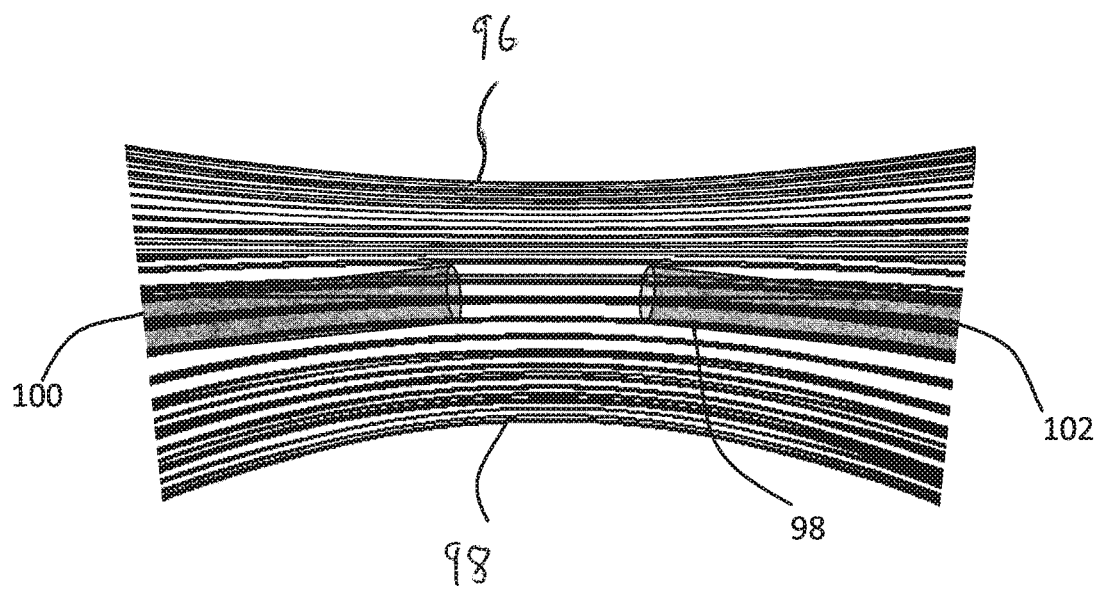
FIG. 7 illustrates a front view of the contoured roller of the liquid applicator device of FIG. 2 in an exemplary second configuration via the axle portions thereof according to the present disclosure.

The effect of the orientation of axle portions 36 is shown in FIGS. 7A and 7B. As shown in FIG. 7A, orienting or bending axle portions 36 (e.g. via hinges 34 and 38) along axes 92 and 94 that are angled inwardly towards the frame 14 inside a cavity 90 of a concave curved roller would bend the roller material (e.g., flexible or elastic material) such that its outer surface is more curved on the front face portion 86 than on a back-face portion 88. In a similar fashion, as shown in FIG. 7B, orienting or bending axle portions 36 (e.g. via hinges 34 and 38) along axes 100 and 102 that are angled outwardly away from the frame 14 inside a cavity 98 of a concave curved roller would bend the roller material (e.g., flexible or elastic material) such that its outer surface is less curved on the front face portion 96 than on a back-face portion 98. The concavity of such a curved roller may thereby depend on the portion thereof that is used (i.e., rolled or dragged) on the surface that the liquid is being applied on/to. Further, the orientation of the axle portions 36 (e.g. via hinges 34 and 38) may be changed or selectively configured based on a particular use or need.

FIG. 8A to 8C illustrate exemplary embodiments of the profile of the outer surface and/or ridges on the surface of the roller. As shown in FIG. 8A, an exemplary roller may include triangular ridges 108 on the outer surface thereof when viewed from the side. The circumference of the roller may be larger on the sides and smaller in the middle of the longitudinal aspect of the roller so that the surface at the medial portion 106 can also be viewed. As shown in FIG. 8A, the roller may include a (circular) cavity or aperture 104 in the center or middle of the roller where the axle portions 36 are inserted. As shown in FIG. 8B, another exemplary roller may include trapezoidal ridges 110 are seen in side view. In FIG. 8C, another exemplary roller may include rectangular ridges 118. The roller may be uniformly formed of an absorbed material. As also shown in FIG. 8C, a roller may be formed of two concentrically arranged materials with the elasticity, porosity and/or flexibility of a core portion 116 being different than that of a surface portion 112. In some such embodiments, the core portion 116 may be less absorbent than the surface portion 112. In some other embodiments, the ridges 118 made be formed of the material as the surface portion 112. The opening 114 in the center of the roller may be configured accept the axle portions 36, upon which the roller rotates when pushed in contact with a surface, as explained above.

Figure 9:
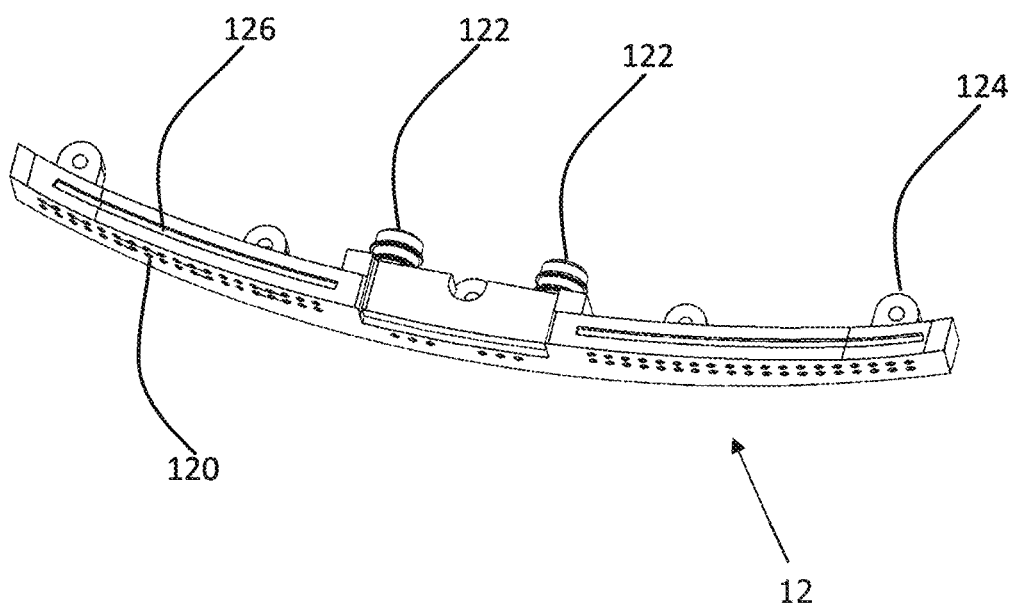
FIG. 9 illustrates an elevational perspective view of an exemplary applicator plate of the liquid applicator device of FIG. 2 according to the present disclosure.

FIG. 9 illustrates an exemplary perforated plate 12. As shown in FIG. 9, at least the forint face of the plate 12 may be convex to conform to a concavity of a roller 10. When the contour of the roller is different, the shape of the perforated plate 12 may also be different to correspond or extend substantially parallel to the outer surface of the roller 10. In one exemplary embodiment, the front face of the perforated plate may include an array of holes 120 that are in direct communication through a channel 126 inside the perforated plate 12 with nipples 122 where the tubes or conduits leading from the container 20 are connected, as shown in FIG. 9. The reservoir of the container 20 may thereby be in fluid continuity with the holes 120 of the perforated plate 12. In some embodiments, the holes 120 are unevenly distributed along the front surface of the plate 12. For example, holes nearer to the nipples 122 may be smaller or less densely spaces than the holes 120 positioned away from the nipples 122, thereby causing the liquid to flow through the holes 120 substantially uniformly when the liquid in the container 20 is pressurized. In one embodiment, the perforated plate 12 may be coupled to the frame 12 by a plurality of fasteners 124 that hold the plate 12 in place, such as one or more screws, or via welding or gluing.

Figure 10:
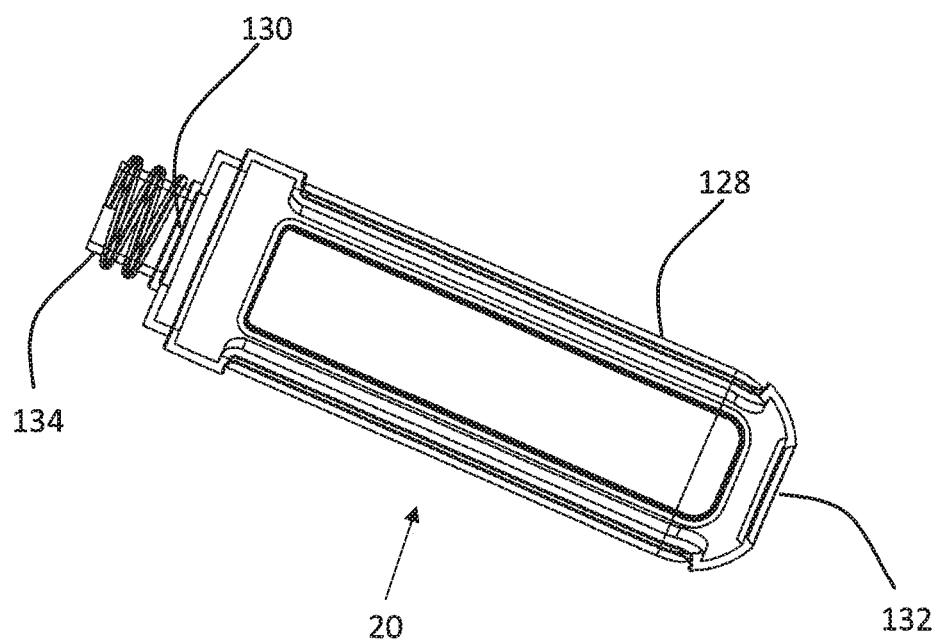
FIG. 10 illustrates an elevational perspective view of an exemplary container-handle of the liquid applicator device of FIG. 2 according to the present disclosure.
Figure 11:
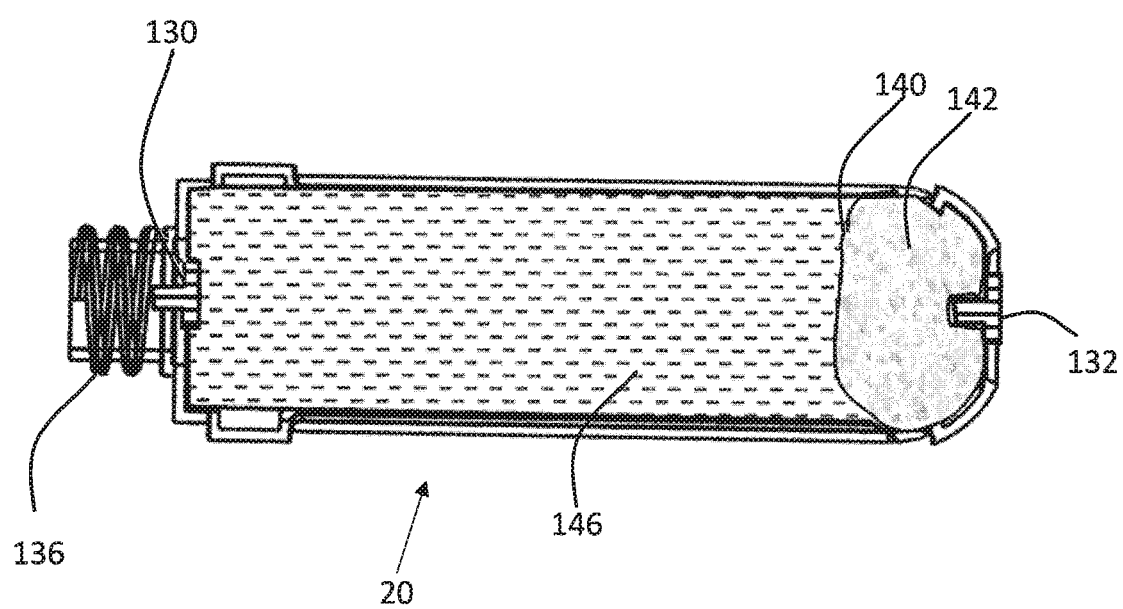
FIG. 11 illustrates a side cross-sectional view of the container-handle of FIG. 10 according to the present disclosure.

FIGS. 10 and 11 illustrate an exemplary container 20. As shown in FIGS. 10 and 11, the container 20 may comprise a flexible, elastic bottle or vessel 20 that defined an internal cavity. In some embodiments, the container 20 may include a threaded neck 134. The threaded neck 134 may fasten the container 20 into the corresponding female thread in the insert 54 to securely hold the container 20 in place while maintaining liquid continuity. In some embodiments, side walls forming the reservoir may be reinforced by ribs 128, which may help to secure the grip of a user and/or to facilitate better recoil or resiliency of the container 20 after it has been deformed or squeezed and the released.

As shown in FIG. 11, the container 20 may include at least a pair of one-way valves that allow only unidirectional flow through them. As shown in FIG. 11, the container 20 may include a dispensing one-way valve 130 may be fitted into the neck 134 of the container 20, such as but not limited to after it has been filled with liquid. The dispensing one-way valve 130 allows only for flow out of the reservoir of the container 20. As shown in FIG. 11, the container 20 may also include an intake second valve 132 fitted into the bottom of the reservoir and only allows for flow of air indirectly into the reservoir, such as directly into a soft-wall impermeable expandable bladder, bag or vessel 140 that is positioned within the internal cavity/reservoir. The volume of the container may be substantially the same as the maximum internal volume of the bladder. The expandable bladder 140 may initially empty or in a collapsed state. After the container/reservoir 20 is deformed or otherwise pressurized so that liquid flows out of the reservoir via the dispensing valve 130, the container 20 may be allowed to elastically or otherwise deform towards its natural state/shape/configuration such that the volume of the reservoir is expanded and thereby forms a vacuum that causes the bladder 140 to draw air or the environment about the device through the intake valve 132 and into the bag 140 to expand the bladder 140 with a volume of internal air 142 equal to the volume of the liquid that was dispensed from the reservoir (and thereby onto the roller).

Figure 12:
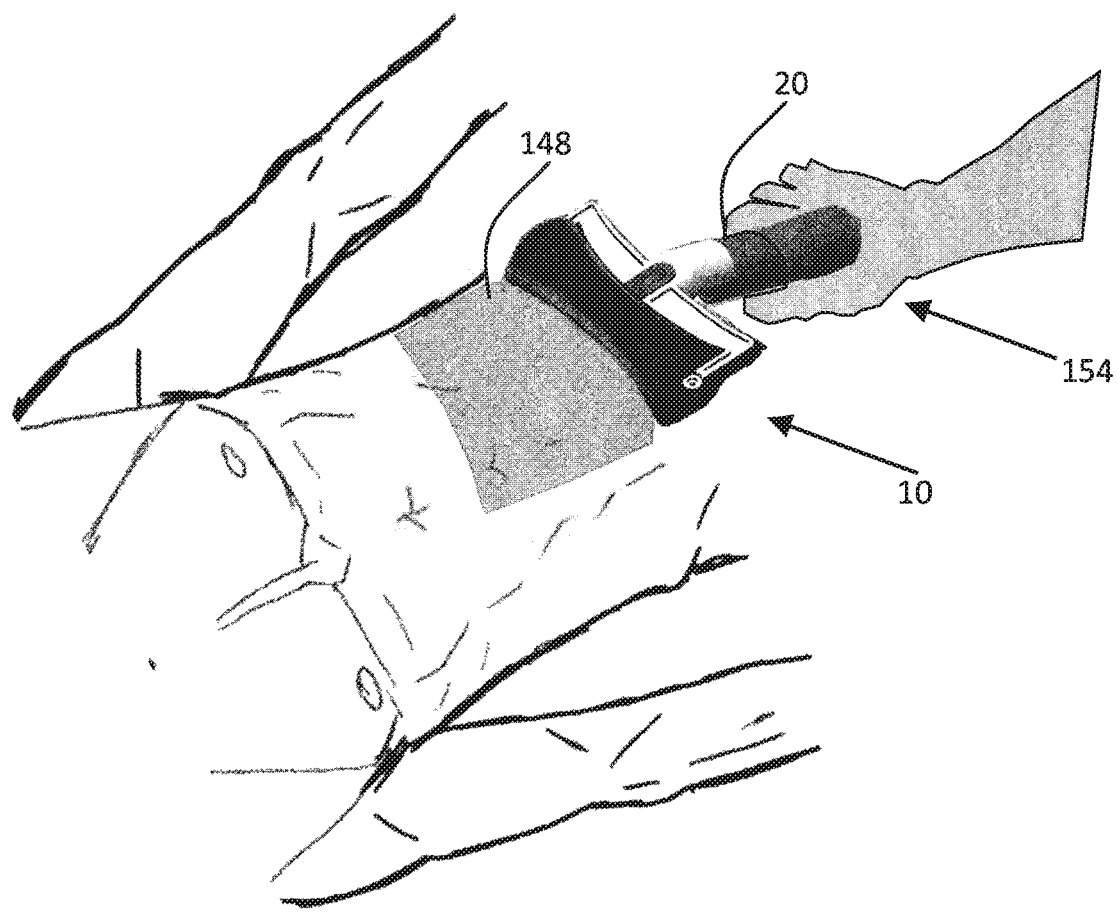
FIG. 12 illustrates an elevational perspective view of the liquid applicator device of FIG. 2 applying liquid disinfectant to an exemplary area of the skin of a patient that includes one or more arcuate surface portions according to the present disclosure.

As shown in FIG. 12, a curved roller 10 of a liquid (medicament) applicator device disclosed herein may be utilized to spread or apply a liquid (medicament) on the skin of a patient 148 by holding the container 20 in the hand of the operator or user 154. The container 20 may thereby be used as a handle, and can be manually squeezed, occasionally or selectively, to force liquid out of the reservoir and onto the roller 10 to sufficiently and evenly coated the skin. It is clear that although the use of a curved roller 10 to spread a liquid on the skin of a patient 148 is illustrated by way of example, the device and the methods of using the device can be used to spread any liquid of any viscosity on any surface via a roller of any shape or configuration, such as for painting, applying cement or smoothing the surface thereof.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has" and "having"), "include" (and any form of include, such as "includes" and "including"), "contain" (and any form contain, such as "contains" and "containing"), and any other grammatical variant thereof, are open-ended linking verbs. As a result, a method or article that "comprises", "has", "includes" or "contains" one or more steps or elements possesses those one or more steps or elements, but is not limited to possessing only those one or more steps or elements. Likewise, a step of a method or an element of an article that "comprises", "has", "includes" or "contains" one or more features possesses those one or more features, but is not limited to possessing only those one or more features.

As used herein, the terms "comprising," "has," "including," "containing," and other grammatical variants thereof encompass the terms "consisting of" and "consisting essentially of."

The phrase "consisting essentially of" or grammatical variants thereof when used herein are to be taken as specifying the stated features, integers, steps or components but do not preclude the addition of one or more additional features, integers, steps, components or groups thereof but only if the additional features, integers, steps, components or groups thereof do not materially alter the basic and novel characteristics of the claimed compositions or methods.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

Whenever a numerical range is indicated herein, it is meant to include any cited numeral (fractional or integral) within the indicated range. The phrases "ranging/ranges between" a first indicated number and a second indicated number and "ranging/ranges from" a first indicate number "to" a second indicated number are used herein interchangeably, and are meant to include the first and second indicated numbers and all the fractional and integral numerals therebetween. As such, where one or more ranges are referred to throughout this specification, each range is intended to be a shorthand format for presenting information, where the range is understood to encompass each discrete point within the range as if the same were fully set forth herein.

All publications, patents and patent applications mentioned in this specification are herein incorporated in their entirety by reference into the specification, to the same extent as if each individual publication, patent or patent application was specifically and individually indicated to be incorporated herein by reference. Subject matter incorporated by reference is not considered to be an alternative to any claim limitations, unless otherwise explicitly indicated. In addition, citation or identification of any reference in this application shall not be construed as an admission that such reference is available as prior art to the present invention. To the extent that section headings are used, they should not be construed as necessarily limiting.

While several aspects and embodiments of the present invention have been described and depicted herein, alternative aspects and embodiments may be affected by those skilled in the art to accomplish the same objectives. It is evident that many alternatives, modifications and variations will be apparent to those skilled in the art. Accordingly, this disclosure and the appended claims are intended to embrace and cover all such further and alternative aspects, modifications, variations and embodiments that fall within the spirit and scope of the invention, disclosure and/or the appended claims.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

The invention claimed is:

1. A liquid disinfectant applicator device, comprising:
   (a) a frame;
   (b) a pair of axle portions that are movably coupled to the frame at varying angles therebetween;
   (c) an absorbable roller rotatably mounted on the pair of axle portions comprising a curved outer surface and an axis of rotation;
   (d) a sealed resilient container coupled to the frame comprising an internal reservoir with a first volume at a natural state of the container for containing a liquid, a one-way dispensing valve in communication with the reservoir configured to only allow for the flow of liquid out from the reservoir, an intake one-way valve in communication with the reservoir, and a soft-walled expandable bladder positioned within the reservoir of the container and sealed to the one-way intake valve, the one-way valve intake being configured to only allow for the flow of air into the expandable bladder;
   (e) at least one conduit in communication with the dispensing valve configured to receive and direct a flow of the liquid therefrom; and
   (f) a perforated plate comprising an array of holes in communication with the at least one conduit and proximate to the roller to deliver the flow of the liquid to the outer surface of the roller;
   (g) wherein a compressive force applied the container deforms the container such that the volume of the reservoir is decreased from the first volume to a second volume and a flow of the liquid is forced through the dispensing valve and to the outer surface of the roller via the at least one conduit and perforated plate, and
   (h) wherein the resiliency of the container causes the container to deform after the compressive force is applied such that the volume of the reservoir is increased from the second volume to the first volume and air is drawn into the expandable bladder via the intake valve.

2. The liquid applicator device of claim 1, wherein the curved outer surface of the roller is curvilinear.

3. The liquid applicator device of claim 1, wherein the curved outer surface of the roller is concave along the axis of rotation thereof.

4. The liquid applicator device of claim 1, wherein the curved outer surface of the roller is convex along the axis of rotation thereof.

5. The liquid applicator device of claim 1, wherein a radius of curvature of the curved outer surface of the roller varies according to the varying angles of the pair of axle portions.

6. The liquid applicator device of claim 1, wherein at least the curved outer surface of the roller comprises open-cell foam.

7. The liquid applicator device of claim 1, wherein the curved outer surface of the roller is smooth.

8. The liquid applicator device of claim 1, wherein the curved outer surface of the roller is serrated with triangular ridges in profile extending along the axis of rotation and spaced about the axis of rotation.

9. The liquid applicator device of claim 1, wherein the curved outer surface of the roller is serrated with trapezoidal ridges in profile extending along the axis of rotation and spaced about the axis of rotation.

10. The liquid applicator device of claim 1, wherein the curved outer surface of the roller is serrated with rectangular ridges in profile extending along the axis of rotation and spaced about the axis of rotation.

11. The liquid applicator device of claim 1, wherein the roller is uniformly formed of an absorbed material.

12. The liquid applicator device of claim 1, wherein the roller is formed of a plurality of concentric liquid absorbing elastic materials.

13. A liquid disinfectant applicator device of claim 1, further comprising a stopper member movably coupled to the frame, wherein the stopper member is movable between engagement with the roller that prevents rotation thereof about the axis of rotation, and disengagement with the roller that allows free rotation thereof about the axis of rotation.

14. The liquid disinfectant applicator device of claim 1, wherein the first volume of the container is substantially the same as the maximum internal volume of the bladder.

15. The liquid disinfectant applicator device of claim 1, further comprising liquid within the reservoir of the container.

16. The liquid disinfectant applicator device of claim 15, wherein the liquid is a liquid medicament.

17. The liquid disinfectant applicator device of claim 16, wherein the liquid medicament is a liquid disinfectant.

18. The liquid disinfectant applicator device of claim 15, wherein the liquid is a lotion.

19. The liquid disinfectant applicator device of claim 15, wherein the liquid is a paint.

20. The liquid disinfectant applicator device of claim 1, wherein the container forms a manually engageable handle of the device.

* * * * *